United States Patent [19]

Thyagarajan

[11] Patent Number: 4,612,404
[45] Date of Patent: Sep. 16, 1986

[54] PROCESS FOR TREATMENT OF FLUIDS CONTAMINATED WITH POLYCHLORINATED BIPHENYLS

[76] Inventor: Budalur S. Thyagarajan, 4518 Maybrook Woods, San Antonio, Tex. 78249

[21] Appl. No.: 552,291

[22] Filed: Nov. 16, 1983

Related U.S. Application Data

[63] Continuation of Ser. No. 381,312, May 24, 1982.

[51] Int. Cl.³ .................. C07C 37/02; C07C 39/12
[52] U.S. Cl. ................................ 568/730; 568/725; 568/726; 568/739
[58] Field of Search ............. 568/725, 724, 726, 730, 568/739

[56] References Cited

U.S. PATENT DOCUMENTS

| | | | |
|---|---|---|---|
| 2,914,558 | 11/1959 | Cooper | 568/739 |
| 3,179,703 | 4/1965 | Rieman | 568/749 |
| 3,597,351 | 8/1971 | Landenburg et al. | 568/724 |
| 4,110,541 | 8/1978 | Kinson | 568/725 |
| 4,191,843 | 3/1980 | Kwantes et al. | 568/724 |
| 4,256,568 | 3/1981 | Schlosberg et al. | 568/749 |
| 4,277,628 | 7/1981 | Carnahan | 568/749 |
| 4,400,552 | 8/1983 | Pytlewski et al. | 568/739 |

FOREIGN PATENT DOCUMENTS 982532 2/1965 United Kingdom ................ 568/724

*Primary Examiner*—Werren B. Lone
*Attorney, Agent, or Firm*—Hubbard, Thurman, Turner & Tucker

[57] ABSTRACT

Polychlorinated biphenyls present as contaminants in fluids such as petroleum distillates are effectively removed by reacting with sodium or potassium hydroxide in the presence of or through subsequent filtration through an adsorbent such as alumina and/or diatomaceous earth. A mixture of diatomaceous earth, calcium hydroxide and potassium hydroxide in the ratio of 10/1/1 is exposed to the fluid to be decontaminated by stirring a quantity of the mixture in a quantity of the fluid or by passing the fluid through a column packed with the mixture. Alternatively, the contaminated fluid is mixed with the alkali metal hydroxide and then passed through a column of adsorbent such as activated basic alumina. The fluid may be pretreated by storing in a tank over a bed of potassium hydroxide flakes. Ferric oxide may be added to the reaction mixture to enhance the retention of the octachlorodihydroxybiphenyl on the adsorbent material.

13 Claims, 1 Drawing Figure

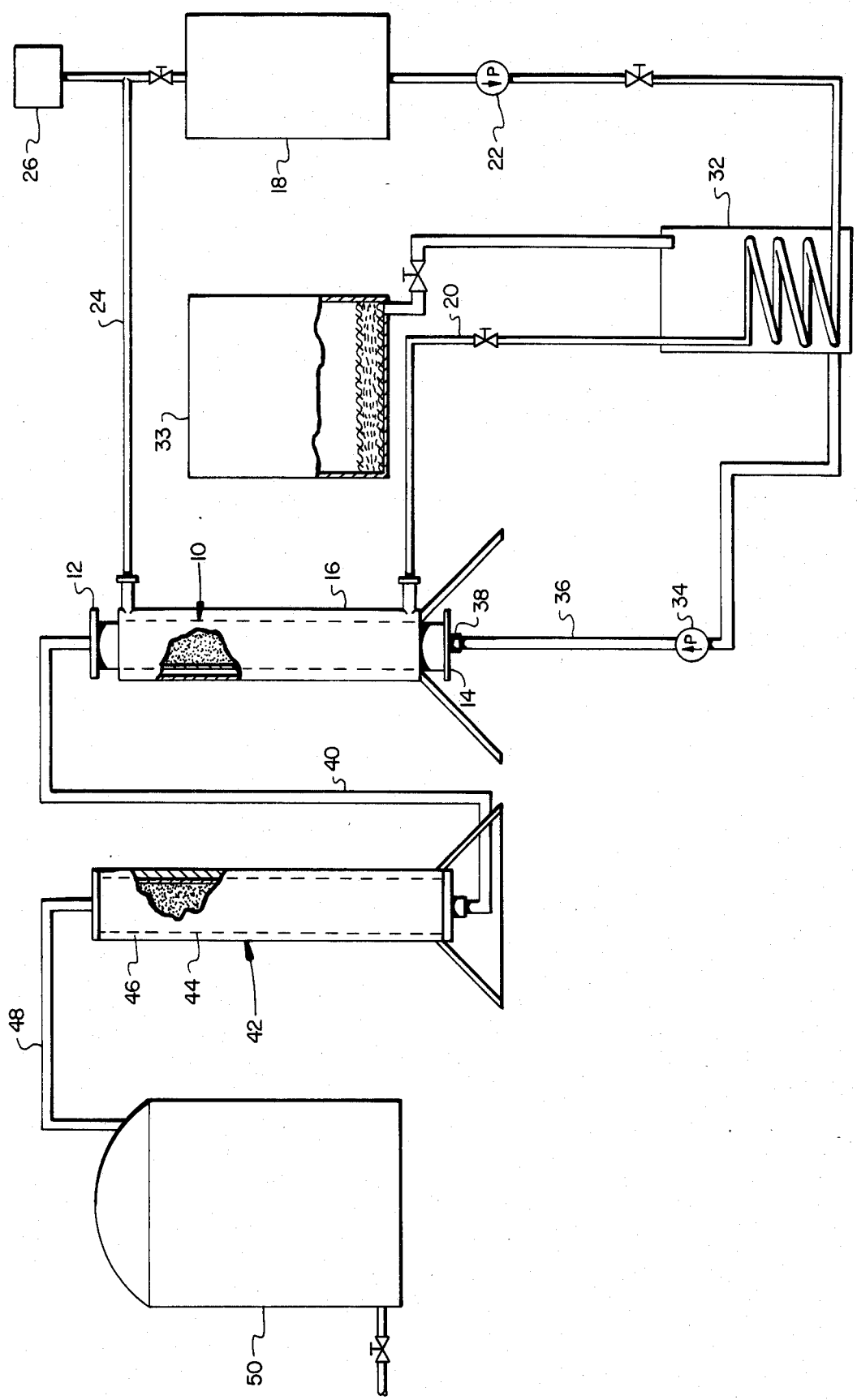

PROCESS FOR TREATMENT OF FLUIDS CONTAMINATED WITH POLYCHLORINATED BIPHENYLS

This application is a continuation of application Ser. No. 381,312, filed May 24, 1982.

BACKGROUND OF THE INVENTION

1. Field of the Invention

The present invention pertains to the treatment of fluids containing polychlorinated biphenyls to convert the toxic compounds to polyhydroxylated biphenyl derivatives and to remove the resultant compounds from fluids such as petroleum base oils and the like.

2. Background Art

The development of polychlorinated biphenyls or PCBs for use as insulating and heat transfer fluids received widespread use until indications of the possibility that these fluids posed a potential health hazard. The use of PCBs in electrical transformers and the like as an insulating and heat transfer fluid has been largely discontinued and even legally banned in some countries. These fluids have been replaced by other fluids including petroleum distillates having properties similar to diesel oil, for example. However, the contamination of large numbers of electrical distribution transformers by the residual amounts of PCBs remaining in the transformer tanks after replacement by other fluids has posed a still further problem in the treatment and disposal of these contaminated fluids. Moreover, the restrictions issued by the U.S. Environmental Protection Agency under the authority of the Toxic Substances Control Act has resulted in the temporary storage of large quantities of PCB contaminated fluids of various types.

The restrictions on the treatment of PCBs has not only posed a dilemma from an environmental standpoint, but has resulted in costly treatment processes for various types of equipment during reconditioning and servicing thereof. In particular, the large number of electrical distribution transformers in use and requiring periodic servicing and reconditioning has posed a substantial problem to the electric utility and electrical equipment manufacturing industry as regards the handling of contaminated transformer oils.

Although several processes for the dechlorination of chlorinated aromatic compounds such as PCBs have been proposed, known processes suffer from several disadvantages including high cost, the use of hazardous materials in the treatment process and requiring complicated equipment and treatment processes. For example, one process which has received some attention includes the mixing of sodium napthalenide with the PCB contaminated fluid followed by distillation to rid the fluid of the residue from the reaction. This method is not only dangerous because it involves the handling of highly reactive sodium metal in the formation of the reagent, but also requires a complicated system for carrying out the treatment of the fluid being decontaminated.

The disadvantages of prior art PCB treatment processes together with the urgent need to deal with the decontamination of large quantities of fluids, particularly of the type used in electrical transformers, has led to the development of the present invention which produces an acceptable reduced level of PCBs in fluids such as petroleum distillates under less hazardous operating conditions and with the fairly simple removal of residues from the fluid wherein the fluid may be recycled for resumption of its intended use.

SUMMARY OF THE INVENTION

The present invention provides methods for dechlorinating polychlorinated biphenyls such as decachlorobiphenyl by reacting the halogenic compound with an alkali metal hydroxide such as sodium or potassium hydroxide or by reacting the halogenic compound with an alkaline earth metal hydroxide. The process involves the substitution of the 4,4'-chlorine atoms of decachlorobiphenyl with sodium hydroxide or potassium hydroxide, for example.

One embodiment of the present invention is directed to a method for the treatment of fluids containing polychlorinated biphenyls as a contaminant by reacting the halogenic compound with sodium or potassium hydroxide using a solvent such as DMSO, THF, DMF, dioxane, ethylene glycol or sulfolane. Still more particularly, the present invention contemplates the decontamination of electrical transformer oil using sodium or potassium hydroxide in a solution of one of the above-mentioned solvents by mixing the oil with the solution followed by filtering of the oil free of any solvents and washing the oil with enough water to remove the excess alkali.

In accordance with another method of the present invention, PCB contaminated fluid is treated with sodium or potassium hydroxide and the reaction is carried out on a reactive surface including activated lime or silica mixed with the metal hydroxide. The mixture of surface material or adsorbent and alkali metal hydroxide can be packed in a column, for example, through which the PCB containing fluid may be forced, preferably from the bottom of the column to the top.

In accordance with a preferred embodiment of the present invention, the contaminated oil is mixed with only the alkali metal hydroxide in a batch or pot type process and the reactants are then passed through a column containing a filtrant and adsorbent. A particularly preferred adsorbent for the process has been discovered to be activated alumina. Use of alumina is preferred for its surprisingly good adsorbing characteristics and due to the discovery that it may be suitably reactivated after use. Moreover, an excess quantity of alkali metal hydroxide is used in the process and suitably reused on a batch process basis for up to three batches of contaminated oil.

The present invention further contemplates the provision of a process for the treatment of fluids such as transformer oils and the like, to remove polychlorinated biphenyls to an acceptable level which presents a minimum environmental hazard, using a composition of materials including potassium hydroxide, calcium hydroxide and diatomaceous earth mixed together and packed in a column through which the contaminated fluid is forced. The column performs a dual function of providing the reaction substances and the column material can also be the appropriate vehicle for disposal of the dechlorinated biphenyl.

The present invention still further contemplates the provision of a composition of materials for removing polychlorinated biphenyls from transformer oils comprising a combination of a filter medium and reaction surface such as diatomaceous or fuller's earth, crushed limestone, together with potassium hydroxide powder or flakes and ferric oxide, the last mentioned compound being provided as a binding agent. The composition may be mixed with the fluid to be treated by stirring a mixture of the composition in a quantity of the fluid or, preferably, by forcing the fluid through a packed column of the material. The provision of ferric oxide as an additional material in the stripping composition increases the efficiency of removing the PCB from the fluid and chemically binds the dechlorinated biphenyl, which is typically a dihydroxyoctachlorobiphenyl compound and other similar hydroxybiphenyls, and retains such compounds on the column material. Accordingly, the provision of the ferric oxide prevents the modified PCB from being eluted back into the fluid from the column material. The provision of the ferric oxide as a catalyst to retain the degraded PCB on the column material also provides for a relatively safe disposal of the dechlorinated PCB.

Although several examples of inventive processes are given hereinbelow, those skilled in the art will appreciate other superior features and advantages of the present invention upon reading the detailed description which follows.

BRIEF DESCRIPTION OF THE DRAWING

The drawing FIGURE illustrates a schematic diagram of a system for treating petroleum distillates such as transformer oils in accordance with one process of the present invention.

DESCRIPTION OF THE PREFERRED EMBODIMENTS

The present invention involves a procedure for treating fluids containing polychlorinated biphenyls (PCBs) by reacting the halogenic compound with an alkali metal hydroxide, preferably sodium or potassium hydroxide, or an alkaline earth metal hydroxide to remove at least two of the chlorine atoms from the decachlorobiphenyl and replacing by a hydroxyl function. This process may be conducted in a number of ways but in accordance with the present invention several preferred processes are provided for the treatment of petroleum distillates and the like and, in particular, insulating and cooling fluids used in electrical transformers.

The decachlorobiphenyl can be converted to octachlorodihydroxybiphenyl by mixing with sodium hydroxide or potassium hydroxide dissolved in a solvent such as dimethyl sulfoxide (DMSO), tetrahydrofuran (THF), dimethyl formamide (DMF), dioxane, ethylene glycol or sulfolane. These are dipolar aprotic solvents which favor nucleophilic substitution of the chlorine atoms by hydroxide ions. By using an excess of the alkaline metal hydroxide the removal of the 4,4'-chlorine atoms can be accomplishe and the hyroxylate product can be kept in solution as well. The fluid, such as transformer oil which is decontaminated by the process, can then be filtered or distilled off as the preference may be. The residual material from such a process including the excess alkali metal hydroxide and the partially dechlorinated PCB can then be treated in other ways to destructively decompose or otherwise modify the octachlorodihydroxybiphenyl molecule. For example, the further prolonged reaction of octachlorodihydroxybiphenyl with excess alkali metal hydroxide or alkaline earth metal hydroxide will slowly decompose the PCBs to form compounds which are anticipated as being biodegradable.

In accordance with one method contemplated by the present invention the contaminated fluid, such as transformer oil, may be stirred in quantities of several gallons at a temperature of from an ambient temperature of about 22° C. to 70° C. with a solvent solution containing the alkali metal hydroxide. The reaction can be done such that a minimum amount of water is added to the solvent to dissolve the hydroxide and then mixed with the fluid such as transformer oil and stirred and heated at the aforementioned temperature. The reaction can be monitored from time to time by gas chromatography for determination of the remaining quantity of PCB in the fluid. The fluid can then be filtered free of any solids, washed with enough water to avoid the formation of any emulsions to remove the excess alkali metal hydroxide and then dried or distilled. The filtered solids and/or the aqueous solvent can be recycled with more metal hydroxide together with a fresh quantity of PCB containing fluid.

However, the processing of large quantities of petroleum distillates such as electrical transformer oils and the like favors yet a further process in accordance with the present invention wherein the reaction of the alkali metal hydroxide or an alkaline earth metal hydroxide is carried out on a reactive surface such as activated lime or silica mixed with sodium or potassium hydroxide, for example. Still other adsorbent materials which are suitable include diatomaceous earth or fuller's earth. A surprisingly advantageous adsorbent has been disovered to be basic alumina. The alkali metal hydroxide may be mixed directly with a quantity of fluid to be treated by stirring the mixture in a vessel containing the fluid, then adding a quantity of adsorbent to the vessel.

Alternatively, the contaminated fluid can be pumped through a packed column containing a quantity of the reaction material and the adsorbent or the fluid may be first treated with the alkali metal hydroxide by the stirring or pot method and then allowed to flow through a bed of adsorbent. The last mentioned process works well for treating contaminated oils with potassium hydroxide as the reaction material and basic alumina as the adsorbent. The surface reaction is effective and the column can be interchanged with a fresh column periodically as soon as the column material becomes saturated with the octachlorodihydroxybiphenyl. The column material itself can become a reaction bed for further decomposition of the octachlorodihydroxybiphenyl, if required. Moreover, the column method favors the use of alkali ion exchange resins which are industrially cheaply produced, have a reliable and consistent quality in manufacture and may perform more uniformly on the column.

In accordance with the present invention, the provision of particular substances, as will be described further herein, produces or aids in producing certain reactions and processes which result in decontamination and purification of petroleum distillates particularly of the type used as transformer oils. Electrical transformer oils become contaminated with PCB as a result of being used in a transformer tank formerly containing an askarel or similar insulating fluid. Transformer oils often become contaminated with quantities of water above a specified level desired for further service. The acidity of the oil may also be at a sufficient level to warrant increasing the pH of the oil before actual treatment to reduce the PCBs. In accordance with the present invention, it is contemplated that a quantity of oil to be treated is sampled for determination of the concentration of PCB by any known method, including gas chromatography. The quantity of oil to be treated is then stored in a vessel over a bed of potassium hydroxide powder or flakes for a period of from 24 to 48 hours to insure that the acidity of the oil is neutralized before commencing the treatment, and, since potassium hydroxide is deliquescent, the water content of the quantity of oil to be treated may also be reduced.

After the pretreatment process, the quantity of oil to be decontaminated may then be thoroughly mixed with a quantity of potassium hydroxide and adsorbents such as basic alumina, or fuller's earth and hydrated limestone or calcium hydroxide. Although calcium hydroxide can participate chemically in the PCB conversion process, it can be less efficient than potassium hydroxide. The presence of the calcium hydroxide does however, augment the surface area available for the reaction and improves the alkalinity to a preferred range of 9 to 12 pH.

The composition to be stirred with the quantity of fluid to be treated or packed in a column through which the fluid is pumped may also incorporate a quantity of ferric oxide which is believed to be suitable to chemically bind the dihydroxyoctachlorobiphenyl for retention on the adsorbent to prevent the modified PCB from being washed back into the fluid being treated. Other chelating compounds which may be used include ferric, manganese and chromium salts. The retention of the PCB on the fuller's earth-limestone solid material provides for safe disposal of the halogenic compound after its chemical modification. This material is, quantitatively, easily handled and disposed of as compared with the substantial quantities of oil or other fluids contaminated with PCBs. Of course, the economic advantages of reconditioning petroleum distillates and the like are noteworthy when compared with the costs of the materials used in the decontamination process.

In accordance with the present invention, tests have been conducted with three basic methods, the pot method, the column method and a combination of both the pot and column methods. Basic advantages of the present invention are present in all methods. All methods do not require the use of a hazardous reactive metal or an inert atmosphere, as required with the use of metallic sodium and napthalene in accordance with prior art methods. The removal of the octachlorodihydroxybiphenyl material is inherent in the substitution reaction itself. That is, the product of substitution is an alkali soluble material. Disposal of the octachlorodihydroxybiphenyl can be effected after it accumulates in large quantities, at which time the waste material itself can become a part of a system for further degradation through use of an excess of sodium hydroxide or potassium hydroxide in the initial process. The method is faster and more economical in that the stripping or purification of fluids such as transformer oils do not require distillation after the treatment process.

Tests with laboratory quantities of contaminated transformer oil using a one pot method have been carried out in accordance with the following procedure. One liter of contaminated transformer oil was placed in a combination heating mantle/magnetic stirrer and heated to 62° C. A mixture of potassium hydroxide and fuller's earth was then added consisting of 2.240 grams of potassium hydroxide blended into 100 grams of earth. The contents of the flask were continuously agitated by magnetic stirring and the oil was sampled at 30 minute intervals by extraction of 50 ml per sample. Each sample extracted was cleaned through a column of clean diatomaceous earth (column diameter 0.75 in., column depth 6 in.). The original concentration of PCB in the oil sample was 149 ppm and the pH of the original oil was approximately 4. Samples taken ½ hour and 1½ hours after commencing the reaction indicated a reduction in PCB to approximately 107 ppm.

Although the aforedescribed pot method has proved the efficacy of the basic process in accordance with the present invention, it is considered desirable for treating relatively large quantities of fluids, such as transformer oils, to provide a more continuous flow type of process and to provide a stationary surface for the reaction and for retention of the reaction products. In accordance with a further example, a system, as illustrated schematically in the drawing FIGURE, was developed for the treatment of fluids such as transformer oil by pumping the contaminated oil through one or more packed columns of adsorbent including the reagent dispersed throughout the adsorbent material.

Referring to the drawing FIGURE, there is illustrated a system for treating fluids contaminated with PCBs and the like including a closed tank, generally designated by the numeral 10, characterized by a vertically arranged cylindrical vessel or column having a nominal inside diameter of approximately 6 inches and a nominal length of approximately 5 feet. The column 10 is closed at both ends by suitable flanges 12 and 14. The column 10 is also provided with a water jacket 16 surrounding the exterior wall of the tank and providing an annular flow path for circulating heated water or other heat transfer fluids therethrough. For example, the water jacket 16 may be connected to a source of heated water such as a heater 18 for receiving hot water through a flow line 20 by way of a pump 22. Water is returned to the heater 18 by a return line 24 leading from the jacket 16. The closed circuit water heater system may also include an expansion tank 26.

Prior to processing the oil through the system illustrated in the drawing FIGURE, the oil is preferably stored in a tank 33 over a bed of potassium hydroxide technical flakes in accordance with a preferred procedure as described hereinbove. Contaminated oil from the tank 33 may then be pumped from the bottom of the tank, passing through the bed of potassium hydroxide to a heat exchanger tank 32 and then by means of a pump 34 through a flow line 36 to an inlet fitting 38 on the bottom flange 14 of the column 10. Treated oil leaving the column 10 is piped by way of a flow line 40 to a second column, generally designated by the numeral 42, which includes an elongated cylindrical tank 44 provided with an insulation jacket designated by the numeral 46. The column 42 is not provided with a heating jacket but is insulated to retain the temperature of the fluid being pumped therethrough at a level close to the preferred treating temperature. Oil treated in the column 42 is then conducted by way of a flow line 48 to a storage tank 50. Oil entering the storage tank 50 is substantially purified and ready for its intended use.

It has been determined in accordance with the present invention that it is relatively important that the flow path of the oil passing through the columns 10 and 42 be from the bottom of the columns to the top. The proportions of the columns 10 and 42 with respect to each other appears to be relatively unimportant. The second column may, for example, have an interior dimension of the tank of approximately 4 inches and be 6 feet in length.

In one test using the system substantially as shown in the drawing FIGURE, both columns were packed with a mixture of diatomaceous earth, potassium hydroxide flakes, and powdered hydrated lime (calcium hydroxide). The ratio of earth to potassium hydroxide to lime was 10/1/1 using 50 lbs. of earth, 5 lbs. of potassium hydroxide, and 5 lbs. of lime. It should be noted that care must be taken to prevent moisture contact with the potassium hydroxide and accordingly, the mixture must be maintained sealed prior to placement in the columns. Steady state temperature conditions measured at the tank 32 were approximately 53° C. Flow through the columns was maintained at approximately 350 ml/min. The oil being treated was originally contaminated with 71 ppm polychlorinated biphenyls. Residence time for the oil in the columns was calculated to range from 8 minutes to 23 minutes based on the flow rate through the columns. Gas chromatography analysis of samples of oil out of the second column indicated as low as 37 ppm of polychlorinated biphenyls resulting in a 48% reduction.

The temperature of the oil at the outlet of the second column averaged approximately 47° C. and the pH of the oil before injection into the columns averaged approximately 6.

The results obtained with the aforedescribed column processes indicated that a further desired reduction in the level of contaminant may be obtainable. Accordingly, additional pot experiments were conducted using oil with higher concentrations of PCB and reacting the contaminated oil with only the alkali metal hydroxide. In two separate tests, 100 ml samples of oil containing 2146 ppm of Aroclor 1242 were placed in a 250 ml round bottom flask. The oil was heated to approximately 71° C. to 75° C. and 15 grams of powdered potassium hydroxide were added to the oil. The oil-potassium hydroxide mixture was agitated by a magnetic stirrer for approximately 15 minutes. At the end of the agitation period, the mixture was poured into a chromatographic tube which contained 25 grams of alumina for filtration and adsorption. The quantity of oil taken off through the adsorbent indicated a PCB concentration of only 78 ppm and 24 ppm in the respective tests. However, there are some indications that prolonged exposure to the adsorbent may cause the concentration of PCB to increase from the minimum value obtainable.

In another experiment, a 100 ml quantity of oil containing 2146 ppm of Aroclor 1242 was mixed with 15 grams of potassium hydroxide at an ambient temperature of 22° C. and agitated for 5 minutes. After agitation of the mixture of contaminated oil and potassium hydroxide, 10 grams of alumina were added to the pot. Agitation was continued for another two minutes, solids allowed to settle, and then the liquid was charged to a chromatographic tube containing 25 grams of alumina having a pH of 8-9. A sample taken from the first 5 grams of oil processed through the alumina indicated a reduction of contaminant PCB to 88 ppm.

In a yet third modification of the pot process, a quantity of 100 ml of oil containing 2146 ppm of Aroclor 1242 was mixed with 15 grams of potassium hydroxide and agitated for 15 minutes. The starting temperature of the oil sample was 70° C. and the oil temperature at the end of the agitation period was 67° C. Upon cessation of the agitation process, the oil was filtered through a column containing 50 grams of alumina. The adsorbent bed, however, also included a layer, on top of the alumina, consisting of a mixture of 10 parts fuller's earth and one part calcium hydroxide. The flow of oil through the column indicated a much greater rate than previous column experiments and samples of oil processed indicated a contamination level of only 195 ppm.

The encouraging results obtained from the above described pot processes using alumina as the adsorbent, served as a basis for conducting further tests using 100 ml quantities of oil containing approximately 2146 ppm of Aroclor 1242 heated to a temperature of 80° C. and stirred with varying quantities of powdered potassium hydroxide ranging from a quantity of 12 grams down to a quantity of 6 grams. The combination of 100 ml quantities of heated oil and potassium hydroxide powder at quantities of 12 g, 10 g, 8 g and 6 g of potassium hydroxide, respectively, were stirred for 30 minutes each. After mixing in the alkali metal hydroxide, the treated oil was divided into equal portions of approximately 50 ml and filtered through respective chromatographic tubes containing 35 g of activated basic alumina having an activity level one and in powder form of 80-200 mesh. The treated oil samples were allowed to gravity flow through the adsorbent and the oil was subjected to a second filtration through a plain glass tube containing 5 g of the same type of alumina. Samples taken from filtrate of each tube indicated a reduction in PCB contamination to a level of 36 ppm and 42 ppm, respectively, for the filtrates from the chromatographic tubes and a contaminant level of only 8 ppm and 2 ppm for the filtrates subjected to the secondary filtration through the tubes containing 5 g of adsorbent.

The above described tests using activated basic alumina as the adsorbent indicated that a mass ratio of alkali metal hydroxide to adsorbent of approximately 0.06 produced the greatest reduction in PCB contamination of the fluid, in fact, to a substantially negligible quantity.

The success with the process described herein for removing Aroclor 1242 from electrical transformer oil, lead to the development of a series of tests for quantities of transformer oil containing approximately 500 ppm Aroclor 1260. Samples of 100 ml quantities of contaminated oil were heated to 80° C. and respective quantities of powdered potassium hydroxide of 12 g, 10 g, 8 g and 6 g were stirred into the liquid for approximately 30 minutes in each case. The treated oil was then filtered in 50 ml quantities through chromatographic tubes containing 50 grams of the activated basic alumina. Chromatographic analysis of the filtrate indicated that after a first filtration, the quantity of residual PCB's ranged from 390 ppm (average) for the samples in which 12 g of potassium hydroxide were mixed to an average of 15 ppm or less of contaminant remaining in the filtrate of the samples in which 6 g of potassium hydroxide per 50 g of adsorbent was used. Accordingly, evidence from the abovementioned tests indicates that a mass ratio of alkali metal hydroxide to adsorbent of approximately 0.06 produces a substantially complete elimination of contaminant from a filtrate in accordance with the above process. This ratio is indicated as being important with respect to the observation that the reactant, when mixed with the contaminated oil, produces a residue or sludge which can foul the adsorbent and accordingly, the lower quantity of reactant produces less residue in the treated liquid.

The above described tests using alkali metal hydroxides as the reactant and activated basic alumina as the adsorbent indicate that the duration of treatment of contaminated petroleum distillates and the like need only be approximately 30 minutes or less at temperatures in the range of 24° C. to 80° C. even when the PCB content is in the range of 2000–2500 ppm. Substantially shorter or longer durations of treatment may be utilized if concentrations of PCB are lower or greater than 2500 ppm, respectively, or depending on the particular askarel being treated. Following the alkali treatment, the treated liquid can be filtered without prior cooling through the adsorbent utilizing gravity filtration or possibly a slight vacuum might be applied to pull the liquid through the adsorbent bed. The above described process can be effected utilizing relatively simple equipment requiring only simple flasks, drums or other containers.

Further tests were conducted with a view to determining if the alkali metal hydroxide, namely potassium hydroxide, could be reclaimed and reused in subsequent batch processes after an initial treatment of a quantity of contaminated transformer oil. Using quantities of 6 g of potassium hydroxide flakes mixed with 100 ml quantities of transformer oil contaminated with 2117 ppm of Aroclor 1242, the initial quantity of oil was thoroughly mixed in a vessel for 30 minutes at approximately 24° C. After mixing, the treated oil was decanted to separate the oil from the potassium hydroxide flakes which were then rinsed with 20 ml of petroleum ether and air dried. After rinse, the same quantity of potassium hydroxide flakes was mixed with a second 100 ml sample of oil contaminated with the same concentration of Aroclor 1242.

A first 50 ml sample of contaminated oil was filtered through 50 g of basic alumina and the filtrate indicated a contamination level of only 10 ppm of PCB. A 50 ml portion from the second 100 ml batch of contaminated oil (which had been treated with the original quantity of potassium hydroxide flakes after the petroleum ether rinse) was filtered through 50 grams of basic alumina yielding a filtrate with a contamination level of only 6 ppm of contaminant. Accordingly, it is evident from the foregoing tests that although a reduced quantity of potassium hydroxide in relation to the adsorbent yields a lower contamination level in the filtrate, this reduced quantity of reactant may be reused with essentially the same results in at least a second reaction. The mass ratio of alkali metal hydroxide to adsorbent is not indicated to be substantially affected by the prior liquid/reactant separation process.

Another significant advantage realizable through the use of an adsorbent such as activated alumina, or basic alumina, is that the adsorbent can be regenerated or reactivated by heat treatment in an oxygen containing atmosphere which simultaneously reactivates the adsorbent surface and eliminates by combustion, all of the adsorbed PCB derived phenolic material. Tests carried out on sample quantities of adsorbent which were heated to 600° F. indicate that suitable reactivation of the alumina is possible. Accordingly, the regeneration of the adsorbent serves not only to destroy the polyhydroxylated phenolic materials, but improves the economy of the process by regenerating substantial quantities of adsorbent.

The foregoing test results indicate that polychlorinated biphenyls may be effectively decomposed by an alkali metal hydroxide such as potassium hydroxide. The experiments lead to the realization that alkaline earth metal hydroxides may also be effective reagents for eliminating PCBs from various oils. Moreover, the test results indicate that the provision of an adsorbent material results in a purification level which may meet environmentally acceptable standards. Although specific examples of the process of the present invention have been given together with examples of further specific improvements in the process, those skilled in the art will appreciate that various substitutions and modifications may be made while utilizing the principles of the present invention and therefore falling within the scope of the invention as expressed in the appended claims.

What is claimed is:

1. A method of treating a quantity of a liquid containing polychlorinated biphenyls as a contaminant in said liquid comprising the step of:
    mixing said quantity of liquid with an alkali earth metal hydroxide selected from Group IIA of the Periodic Table.

2. A method of treating a quantity of a petroleum distillate such as transformer oil and the like containing polychlorinated biphenyl as a contaminant by converting said polychlorinated biphenyl to hydroxylated biphenyl and removing said hydroxylated biphenyl from said oil, comprising the steps of:
    providing a vessel containing a quantity of alkali metal hydroxide selected from a group consisting of sodium hydroxide, potassium hydroxide, and lithium hydroxide and a quantity of an adsorbent selected from a group consisting of diatomaceous earth, fuller's earth, activated silica, activated alumina and crushed limestone;
    heating a quantity of said oil to a temperature in the range of about 22° C. to 77° C.;
    introducing said oil to said vessel and maintaining a residence time of said oil exposed to said alkali metal hydroxide and said adsorbent of at least five minutes to convert said polychlorinated biphenyl to said hydroxylated biphenyl and to remove said hydroxylated biphenyl from said oil; and
    withdrawing said oil from said vessel.

3. The method set forth in claim 2 wherein:
    said adsorbent comprises activated basic alumina and said method includes the step of:
    regenerating said adsorbent by heating said adsorbent to remove adsorbed material including said hydroxylated biphenyl from said adsorbent and to reactivate the adsorbent surface of said adsorbent.

4. The method set forth in claim 2 wherein:
    said alkali metal hydroxide and said adsorbent are thoroughly mixed and packed in said vessel arranged as a column.

5. The method set forth in claim 2 wherein:
    said vessel is arranged as a column and is packed with a lower layer comprising a mixture of diatomaceous earth, calcium hydroxide, and potassium hydroxide, a middle layer comprising a mixture of diatomaceous earth and potassium hydroxide and an upper layer comprising a mixture of diatomaceous earth and calcium hydroxide.

6. The method set forth in claim 2 together with the step of:
    storing said quantity of oil in contact with a quantity of potassium hydroxide for a period of time and then passing said quantity of said oil through said vessel arranged as a column containing said alkali metal hydroxide and said adsorbent.

7. The method set forth in claim 2 wherein:
    the mass ratio of said alkali metal hydroxide to said adsorbent is generally less than 0.17.

8. The method set forth in claim 7 wherein:
    said mass ratio is about 0.06.

9. The method set forth in claim 3 wherein:

said adsorbent is heated to a temperature of at least 600° F. in an oxygen containing atmosphere.

10. The method set forth in claim 5 wherein:
said liquid is passed through said column from the bottom of said column to the top of said column.

11. The method set forth in claim 10 wherein:
said solid material is arranged in discrete layers in said column including a lower layer comprising a mixture of diatomaceous earth, calcium hydroxide and potassium hydroxide, a middle layer comprising a mixture of diatomaceous earth and potassium hydroxide and an upper layer comprising a mixture of diatomaceous earth and calcium hydroxide.

12. A method of decontaminating a water immiscible liquid such as electrical transformer oil and the like to remove polychlorinated biphenyls comprising the steps of:
providing a first vessel containing potassium hydroxide flakes as a bed in said first vessel;
providing a second vessel containing a quantity of potassium hydroxide and an adsorbent selected from a group consisting of diatomaceous earth, fuller's earth and alumina;
introducing contaminated liquid to said first vessel and withdrawing said liquid from said first vessel through said bed;
passing said liquid through said second vessel at a temperature in the range of about 22° C. to 77° C. to react said potassium hydroxide with said polychlorinated biphenyl and to adsorb the reaction product comprising hydroxylated biphenyl onto said adsorbent by maintaining a residence time of said liquid in said second vessel of at least eight minutes; and
withdrawing liquid from said second vessel substantially free of said polychlorinated biphenyl and said reaction product.

13. A method of decontaminating electrical transformer oil and like water immiscible liquids wherein said oil is contaminated with polychlorinated biphenyls, comprising the steps of:
providing a first vessel containing a quantity of potassium hydroxide;
providing a second vessel containing a quantity of alumina;
introducing contaminated liquid into said first vessel and mixing said liquid with said potassium hydroxide at a temperature in the range of about 22° C. to about 77° C. for a period of from five minutes to thirty minutes to convert said polychlorinated biphenyls to hydroxylated biphenyl as a reaction product;
removing said liquid from said first vessel and passing said liquid through said second vessel to filter reaction products from said liquid;
withdrawing said liquid from said second vessel substantially free of polychlorinated biphenyls and reaction products; and
regenerating said adsorbent by heating said adsorbent to about 600° C. to destroy said hydroxylated biphenyls so that said adsorbent can be reused.

* * * * *